(12) United States Patent  
Bunce et al.

(10) Patent No.: US 9,157,923 B2
(45) Date of Patent: Oct. 13, 2015

(54) REAGENT BEAD INSERTER

(71) Applicant: Dynex Technologies, Inc., Chantilly, VA (US)

(72) Inventors: Adrian Bunce, West Sussex (GB); Andrew Fusellier, Bristow, VA (US)

(73) Assignee: Dynex Technologies, INC., Chantilly, VA (US)

( * ) Notice: Subject to any disclaimer, the term of this patent is extended or adjusted under 35 U.S.C. 154(b) by 0 days.

(21) Appl. No.: 14/387,043

(22) PCT Filed: Mar. 6, 2013

(86) PCT No.: PCT/GB2013/050555
§ 371 (c)(1),
(2) Date: Sep. 22, 2014

(87) PCT Pub. No.: WO2013/140128
PCT Pub. Date: Sep. 26, 2013

(65) Prior Publication Data
US 2015/0094238 A1    Apr. 2, 2015

(30) Foreign Application Priority Data

Mar. 21, 2012 (EP) ...................................... 12160511
Mar. 21, 2012 (GB) ................................... 1204891.4

(51) Int. Cl.
*G01N 35/10* (2006.01)
*B01L 3/02* (2006.01)
*B01J 19/00* (2006.01)

(52) U.S. Cl.
CPC ......... *G01N 35/1002* (2013.01); *B01J 19/0046* (2013.01); *B01L 3/021* (2013.01); *B01L 3/0217* (2013.01); *G01N 35/1074* (2013.01); *B01J 2219/00364* (2013.01); *B01J 2219/00416* (2013.01); *B01J 2219/00418* (2013.01); *B01J 2219/00468* (2013.01); *B01L 2200/0642* (2013.01); *B01L 2200/16* (2013.01); *B01L 2400/049* (2013.01); *B01L 2400/0478* (2013.01)

(58) Field of Classification Search
CPC .............. G01N 35/1002; B01J 19/0046; B01J 2219/00457–2219/00468
See application file for complete search history.

(56) References Cited

U.S. PATENT DOCUMENTS

| | | | |
|---|---|---|---|
| 6,074,609 A | 6/2000 | Gavin et al. | |
| 2008/0281466 A1 | 11/2008 | Vann | |
| 2011/0027914 A1* | 2/2011 | Bunce et al. | 436/518 |
| 2012/0183977 A1* | 7/2012 | Bunce et al. | 435/7.92 |

FOREIGN PATENT DOCUMENTS

| | | |
|---|---|---|
| DE | 102010040681 | 3/2012 |
| WO | 00/49382 | 8/2000 |
| WO | 01/76755 | 10/2001 |

* cited by examiner

*Primary Examiner* — Lyle Alexander
*Assistant Examiner* — Matthew Krcha
(74) *Attorney, Agent, or Firm* — Diederiks & Whitelaw, PLC

(57) ABSTRACT

A system for inserting reagent or macrobeads into bores of a sample plate is disclosed comprising an insertion device arranged to retain one or more reagent or macrobeads by means of a vacuum whilst inserting the reagent or macrobeads into bores of the sample plate.

14 Claims, 8 Drawing Sheets

REAGENT BEAD INSERTER

CROSS-REFERENCE TO RELATED APPLICATION

This application is the National Stage of International Application No. PCT/GB2013/050555, filed 6 Mar. 2013, which claims priority from and the benefit of United Kingdom Patent Application No. 1204891.4 filed on 21 Mar. 2012 and European Patent Application No. 12160511.7 filed on 21 Mar. 2012. The entire contents of this application is incorporated herein by reference.

BACKGROUND OF THE PRESENT INVENTION

The present invention relates to a system for inserting reagent or macrobeads into one or more bores of a sample plate and a method of inserting reagent or macrobeads into one or more bores of a sample plate.

A technology has been developed which enables multiple tests to be carried out in a single well of a sample plate. The technology uses macro sized (e.g. mm sized) reagent beads that are coated with specific antigens or antibodies. Each well of a sample plate comprises multiple bores in the base portion of the sample plate. Reagent or macro beads are pressed and retained in the bores of each well by an interference fit so that the top half of bead is within the well and is exposed to the assay test.

U.S. Pat. No. 6,074,609 discloses a system for arraying microbeads. The microbeads disclosed in U.S. Pat. No. 6,074,609 are of the order of 5-300 μm i.e. are an order of magnitude smaller than the macrobeads used according to a preferred embodiment of the present invention. The microbeads are stored in a reservoir holding a liquid medium. A distal end of a transfer member is lowered into the liquid medium and a vacuum is created within a lumen to draw a microbead onto the distal end of the transfer member. The transfer member is then lifted from the reservoir whilst holding the microbead on the distal end. The transfer member is then positioned in a test well holding another liquid medium. The vacuum is then removed and the microbead is released from the transfer member whilst the transfer member is within the liquid medium. The microbead is then allowed to fall under the force of gravity within the liquid medium.

There are a number of problems with the arrangement disclosed in U.S. Pat. No. 6,074,609.

One problem with the arrangement disclosed in U.S. Pat. No. 6,074,609 is that as a microbead is being drawn towards the distal end of the transfer member the lumen will at least partially fill with fluid. This can cause a serious problem with cross-contamination.

Another problem with the arrangement disclosed in U.S. Pat. No. 6,074,609 is that the microbeads and in particular any sensitive coating on the microbeads may become damaged whilst the microbead is being transferred by the transfer member.

It is desired to mass produce sample plates and to improve the process of locating reagent or macrobeads in the bores of a sample plate.

SUMMARY OF THE PRESENT INVENTION

According to an aspect of the present invention there is provided a system for inserting reagent or macrobeads into one or more bores of a sample plate comprising:

an insertion device comprising one or more push or insertion rods;

a cartridge comprising, in use, a plurality of reagent or macrobeads;

a sample plate having an upper surface and a lower surface and one or more bores extending from the upper surface through to the lower surface, wherein the cartridge is located, in use, adjacent and/or below the sample plate; and wherein the insertion device is arranged and adapted:

(i) to cause the one or more push or insertion rods to enter the cartridge so that each push or insertion rod collects and retains a reagent or macrobead by means of a vacuum, suction or a reduced pressure region; and then (ii) to cause each of the one or more push or insertion rods to exit the cartridge and insert each reagent or macrobead into a bore of the sample plate via the lower surface of the sample plate.

The system and method according to the present invention is particularly advantageous compared with the arrangement disclosed in U.S. Pat. No. 6,074,609 and other known arrangements for handling reagent beads.

According to the present invention contact between the insertion device and the reagent beads is with the bottom or underneath portion of the reagent beads so that any witness mark or other damage caused to the reagent bead will also be on the bottom or underneath portion of the reagent bead and not on any portion of the reagent bead which will come into subsequent contact with sample fluid. Also, it does not matter if the tip of the insertion device effectively cross contaminates other reagent beads since the insertion device will only come into contact with the underneath or bottom portion of the reagent beads. The insertion device does not come into contact with the top portion of the reagent beads, namely the portion of the reagent beads which will come into contact with a sample fluid.

The present invention is therefore particularly advantageous compared with conventional arrangements.

The insertion device is preferably arranged and adapted to cause each of the push or insertion rods to insert a reagent or macrobead into a bore of the sample plate so that each reagent or macrobead forms a fluid tight circumferential seal with the bore.

The sample plate is preferably arranged so that, in use, an analyte or other sample when dispensed into the sample plate via the upper surface of the sample plate makes fluid contact with an upper portion of the reagent or macrobead which has not been in direct contact with the one or more push or insertion rods.

The sample plate is preferably arranged so that a lower portion of the reagent or macrobead which has been in direct contact with the one or more push or insertion rods does not make fluid contact with the analyte or other sample when the analyte or other sample is dispensed into the sample plate via the upper surface of the sample plate.

The one or more push or insertion rods preferably comprise one or more internal bores.

The system preferably further comprises a vacuum device arranged and adapted to apply or maintain a vacuum, suction or reduced pressure region at an end of the one or more push or insertion rods or the one or more internal bores in the push or insertion rods so as to retain in use a reagent or macrobead on the end of the one or more push or insertion rods whilst the insertion device is in the process of inserting the one or more reagent or macrobeads into the one or more bores of the sample plate.

The cartridge preferably comprises one or more membranes or retention members provided in the base of the cartridge and wherein, in use the one or more push or insertion rods pass through or past the one or more membranes or retention members.

According to an embodiment in the absence of the one or more push or insertion rods the one or more membranes or retention members close to seal the cartridge and prevent reagent or macrobeads located within the cartridge from exiting the cartridge.

The cartridge preferably comprises a removable cap having one or more apertures wherein the one or more push or insertion rods pass through the one or more apertures in the process of inserting the reagent or macrobeads into the one or more bores of the sample plate.

The cap preferably comprises one or more membranes or retention members and wherein, in use, the one or more push or insertion rods pass through or past the one or more membranes or retention members in the process of inserting reagent or macrobeads into the one or more bores of the sample plate.

The system preferably further comprises a cartridge holder arranged and adapted to hold the cartridge in position relative to the sample plate.

The cartridge preferably comprises an identification symbol or barcode.

The cartridge holder preferably comprises an aperture and the identification symbol or barcode is preferably viewable via the aperture in the cartridge holder.

According to an aspect of the present invention there is provided a method of inserting reagent or macrobeads into one or more bores of a sample plate comprising:

providing a cartridge comprising a plurality of reagent or macrobeads;

providing a sample plate having an upper surface and a lower surface and one or more bores extending from the upper surface through to the lower surface;

locating the cartridge adjacent and/or below the sample plate;

causing one or more push or insertion rods to enter the cartridge so that each push or insertion rod collects and retains a reagent or macrobead by means of a vacuum, suction or a reduced pressure region; and then causing each of the one or more push or insertion rods to exit the cartridge and insert each reagent or macrobead into a bore of the sample plate via the lower surface of the sample plate.

The method preferably further comprises causing each of the push or insertion rods to insert a reagent or macrobead into a bore of the sample plate so that each reagent or macrobead forms a fluid tight circumferential seal with the bore.

The method preferably further comprises dispensing an analyte or other sample into the sample plate via said upper surface of the sample plate so that the analyte or other sample contacts an upper portion of the reagent or macrobead which has not been in direct contact with the one or more push or insertion rods.

The method preferably further comprises arranging the sample plate so that a lower portion of the reagent or macrobead which has been in direct contact with the one or more push or insertion rods does not make fluid contact with the analyte or other sample when the analyte or other sample is dispensed into the sample plate via the upper surface of the sample plate.

A sample plate according to the preferred embodiment is preferably arranged to receive one or more reagent or macrobeads. The bead composition may vary dependent on the type of assay being performed. The beads may be composed of plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles, Teflon or any combination thereof. In one embodiment the beads may comprise polystyrene, plastic, a polymer, or a combination thereof. In another embodiment, the beads may comprise a ferrous or magnetic coating or have a ferrous or magnetic property. In yet another embodiment, the beads may comprise an anti-static coating or have an anti-static property. The beads may be translucent, slightly translucent, or opaque. Commercially available beads may be used.

The beads preferably have a diameter of between 0.1 mm and 10 mm. In one embodiment the beads may have a diameter <0.5 mm; 0.5-1.0 mm; 1.0-1.5 mm; 1.5-2.0 mm; 2.0-2.5 mm; 2.5-3.0 mm; 3.0-3.5 mm; 3.5-4.0 mm; 4.0-4.5 mm; 4.5-5.0 mm; or >5.0 mm.

The beads may have a diameter greater than, equal to, or less than the diameter of a bore of a sample well. For example, the beads may have a diameter less than the diameter of a bore of a sample well, wherein the bore comprises a tapered section. In yet another embodiment, the beads may have a diameter greater than the diameter of a bore of a sample well. For example, the bore may not comprise a tapered section. The diameter of a bead to be deposited, or present, in the sample plate, may be at least about 5, 10, 15, 20, 25, 30, 35, 40, 45, 50, 55, 60, 65, 70, 75, 80, 85, 90, 95, or 100% greater than the diameter of a bore of the sample plate. In one embodiment, the beads present in a sample plate does not touch the bottom of a sample plate, such as a base portion of a sample well.

A bead within the sample plate may comprise a reagent or probe, or may be coated with a reagent or probe. The reagent or probe can be used to analyze a sample, such as by detecting an analyte. The probe or reagent can be attached to the bead. The attachment can be a covalent or non-covalent interaction. The probe can be a nucleic acid, antibody, antibody fragment, protein, peptide, aptamer or chemical compound. For example, the probe may be an oligonucleotide. In one embodiment, the probe can be used to detect an analyte in a biological sample. In yet another embodiment, the probe can be used for drug screening. For example, a library of compounds or antibodies can be screened for its binding ability to a protein or nucleic acid probe.

The probe can be used to detect a biomarker for a diagnosis or prognosis of a disease or condition, drug response or potential drug response, or for monitoring the progression of a disease or condition. For example, the probe may comprise an antibody or fragment thereof that is used to detect an antigen that is a biomarker for cancer. In another embodiment, the probe can be an antigen, peptide or protein, which is used to detect an antibody in a sample, which can be an indicative of a disease or condition.

The sample plate may comprise a plurality of probes, wherein some of the probes differ from other probes. The plurality of probes may be attached to the beads. The different probes can be used to detect different analytes, thus allowing multiplexing with the sample plate. The sample plate may comprise at least 2, 3, 4, 5, 6, 7, 8, 9, 10, 11, 12, 13, 14, 15, 16, 17, 18, 19, or 20 different probes. The probes can be of the same type (for example, different antibodies) or of a different type (for example, a combination of nucleic acid probe(s) and antigen(s)).

According to an aspect of the present invention there is provided a system for inserting reagent or macrobeads into one or more bores of a sample plate comprising:

an insertion device arranged and adapted to retain one or more reagent or macrobeads by means of a vacuum, suction or a reduced pressure region whilst inserting the one or more reagent or macrobeads into one or more bores of a sample plate.

The insertion device preferably comprises one or more push or insertion rods.

The one or more push or insertion rods preferably comprise one or more internal bores.

The system preferably further comprises a vacuum device arranged and adapted to apply or maintain a vacuum, suction or reduced pressure region at an end of the one or more push or insertion rods or the one or more internal bores in the push or insertion rods so as to retain in use a reagent or macrobead on the end of the one or more push or insertion rods whilst the insertion device is in the process of inserting the one or more reagent or macrobeads into the one or more bores of the sample plate.

The system preferably further comprises a sample plate comprising one or more bores.

The system is preferably arranged to locate the sample plate above the insertion device.

The sample plate preferably comprises an upper surface and a lower surface and wherein the insertion device is arranged and adapted to insert the one or more reagent or macrobeads into the one or more bores of the sample plate via the lower surface of the sample plate.

The system preferably further comprises a cartridge comprising, in use, a plurality of reagent or macrobeads.

The system is preferably arranged and adapted to locate the sample plate adjacent and/or above the cartridge.

The insertion device is preferably arranged and adapted to extract one or more reagent or macrobeads from the cartridge and to insert the one or more reagent or macrobeads within the one or more bores of the sample plate.

The cartridge preferably comprises one or more membranes or retention members provided in the base of the cartridge and wherein, in use, the one or more push or insertion rods pass through or past the one or more membranes or retention members.

According to the preferred embodiment in the absence of the one or more push or insertion rods the one or more membranes or retention members close to seal the cartridge and prevent reagent or macrobeads located within the cartridge from exiting the cartridge.

The cartridge preferably comprises a removable cap having one or more apertures wherein the one or more push or insertion rods pass through the one or more apertures in the process of inserting the reagent or macrobeads into the one or more bores of the sample plate.

One or more membranes or retention members are preferably provided in the cap and wherein, in use the one or more push or insertion rods pass through or past the one or more membranes or retention members in the process of inserting reagent or macrobeads into one or more bores of the sample plate.

The system preferably further comprises a cartridge holder arranged and adapted to hold the cartridge in position relative to the sample plate.

The cartridge preferably comprises an identification symbol or barcode.

The identification symbol or barcode is preferably viewable via an aperture in the cartridge holder.

According to an aspect of the present invention there is provided a method of inserting reagent or macrobeads into one or more bores of a sample plate comprising:

retaining one or more reagent or macrobeads by means of a vacuum, suction or a reduced pressure region whilst inserting the one or more reagent or macrobeads into one or more bores of a sample plate.

The preferred embodiment relates to automated equipment which is arranged and adapted to locate or assemble reagent beads into a plurality of bores in sample wells of a sample plate. In particular, a preferred reagent or macrobead insertion device is provided which enables reagent beads to be inserted with an insertion height accuracy of ±0.1 mm across the entire sample plate. The preferred insertion device is also able to insert reagent or macrobeads with an insertion height precision of ±0.1 mm across the entire sample plate. Furthermore, the preferred insertion device is preferably able to insert reagent or macrobeads without damaging the bead surface or coating and without damaging the bead surface or coating which comes into contact with a sample fluid in use.

The preferred bead inserter preferably prevents damaging the beads during the insertion process. The preferred bead inserter also preferably prevents damaging the surface of the reagent beads that will be in subsequent contact with sample fluid when the beads are inserted in the bore of the sample well.

According to an embodiment there is provided a mechanism that picks up and locates reagent beads or macrobeads into a sample plate. The preferred device may be incorporated into various instruments or automated equipment.

According to an embodiment a cartridge containing reagent or macrobeads is provided. The cartridge preferably comprises entry points that allow a reagent or macrobead insertion device or mechanism to go into the cartridge and retain reagent or macrobeads in a controlled manner.

The insertion device may comprise one or more bead insertion rods having ends which preferably allow bead pickup whilst ensuring that the reagent or macrobeads do not get damaged.

A method of engaging and disengaging the insertion rods is disclosed.

A method of connecting and disconnecting vacuum pressure is disclosed.

A method of holding the cartridge in place and allowing the assembly to be removed easily for cleaning is disclosed.

A method of allowing a cartridge identification barcode to be read is disclosed.

BRIEF DESCRIPTION OF THE DRAWINGS

Various embodiments of the present invention will now be described, by way of example only and with reference to the accompanying drawings in which.

DETAILED DESCRIPTION OF PREFERRED EMBODIMENTS

Figure 1:
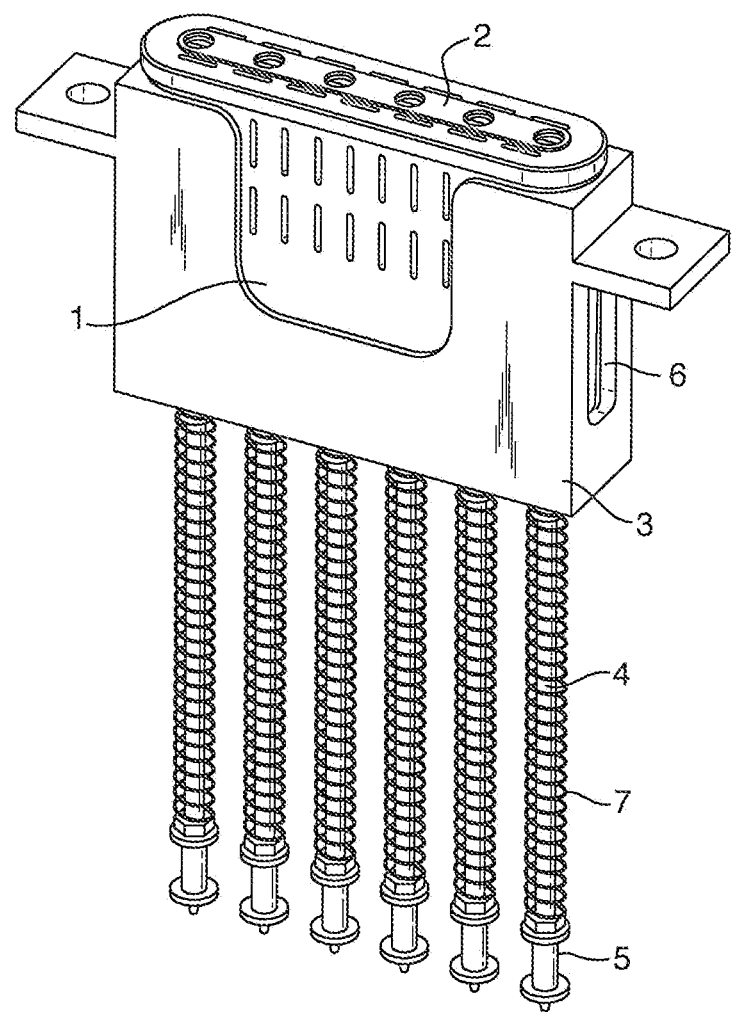
FIG. 1 shows a complete cartridge holding assembly.

A preferred embodiment of the present invention will now be described with reference to FIG. 1. Reagent beads or macrobeads are preferably loaded into one or more cartridges 1 by an operator and may be stored or placed directly on to a preferred reagent bead insertion device. The operator preferably removes an upper cap 2 from the cartridge 1 and pours beads into the cartridge 1 and then replaces the cap 2.

The cap 2 preferably comprises one or more apertures. The operator may apply a strip of tape or another closure device to some or all of the apertures in the cap 2 in order to prevent reagent beads from falling out of the cartridge 1. According to an alternative embodiment holes in the cap 2 may have silicone membranes which prevent beads from falling out.

The operator may apply a barcode label identification on to an end of the cartridge 1. The operator then preferably loads the filled cartridge 1 into a cartridge holder 3. The cartridge holder 3 may be positioned adjacent the insertion device. Alternatively, the cartridge holder 3 may be located distal to the insertion device and the cartridge holder 3 may be manually or automatically positioned adjacent the insertion device. An aperture 6 is preferably provided in the cartridge holder 3 and enables a barcode label on the cartridge 1 to be inspected.

The bead insertion device preferably comprises a plurality of push rods 4 which are arranged so as to engage a lift drive mechanism at a lower end. The bottom or lower ends of the push rods 4 preferably each comprise a connection boss 5. The connection bosses 5 are preferably held securely in the lift drive mechanism so that the push rods 4 are subsequently positively driven linearly in an up and down direction. The bottom face of the connection bosses 5 is preferably arranged to seal to the lift drive mechanism during engagement.

According to a particularly preferred embodiment the push rods 4 preferably comprise one or more axial bores which preferably extend the whole length of the push rods 4. At the lower end of the push rods 4 the bore which extends through the connection bosses 5 preferably allows vacuum pressure to be routed through the push rods 4 to the end of the push rods 5. The vacuum or low pressure region which is preferably created at the upper end of the push rods 4 is preferably used to secure and retain a reagent bead or macrobead on the end of the push rod 4 during an insertion process.

At the base of the bead cartridge 1 one or more preferably soft silicone membranes may be provided which allow the push rods 4 to enter the cartridge 1 without letting the beads fall out of the cartridge 1. As the push rods 4 travel up and through the bead cartridge 1 the push rods 4 preferably each collect a reagent or macrobead on to the end of the push rod 4. According to the preferred embodiment the vacuum pressure preferably sucks a single bead on to the end of each push rod 4 and retains the bead in a defined position on the end of the push rod 4.

According to an embodiment the system is preferably arranged to sense the change in vacuum pressure caused by a bead being sucked on to the end of a push rod 4 and sealing the open end of the push rod 4.

The push rods 4 preferably continue to move up through the cartridge 1 and preferably extend out of the apertures in the cartridge cap 2. A sample plate or macroplate (not shown) is preferably positioned above the cartridge 1 so that specific well pockets or bores in the sample plate are aligned with the push rods 4 coming up through the cartridge 1 and exiting via the cartridge cap 2. The push rods 4 preferably press reagent or macrobeads into bores formed within the sample plate or macroplate via the rear or lower surface of the sample plate or macroplate. The push rods 4 preferably ensure that reagent or macrobeads are inserted into the bores of the sample plate at a desired height. Once reagent beads have been inserted or pressed into the bores of the sample wells, the insertion rods 4 are then preferably driven in the reverse direction and return back down through the cartridge cap 2, the body of the cartridge 1 and the base of the cartridge 1. The push rods 4 are also returned to their pz initial position with the aid of push rod return springs 7. The system is preferably arranged and adapted to determine when reagent beads have been inserted into the bores in the wells of a sample plate and thus when the reagent beads have left the ends of the insertion rods by sensing changes in the vacuum pressure.

According to a preferred embodiment a cycle of inserting reagent beads into the sample wells of a sample plate is preferably repeated one or more times until the sample plate or macroplate is preferably loaded with a desired number of reagent or macrobeads of a first particular type. The system may comprise multiple cartridge holders 3 containing cartridges 1 each containing different specific bead types. The system may insert or fit all desired reagent beads of a first type and then disengage a cartridge holder 3 holding a cartridge 1 containing beads of the first type. The system may then engage a cartridge holder 3 holding a cartridge 1 containing beads of a second different type. The system may insert or fit all desired reagent beads of the second type into the sample plate. This process may be repeated with a third cartridge containing beads of a third different type and/or a cartridge containing beads of a fourth different type etc. until the sample plate is loaded with reagent beads of all desired types.

Figure 2:
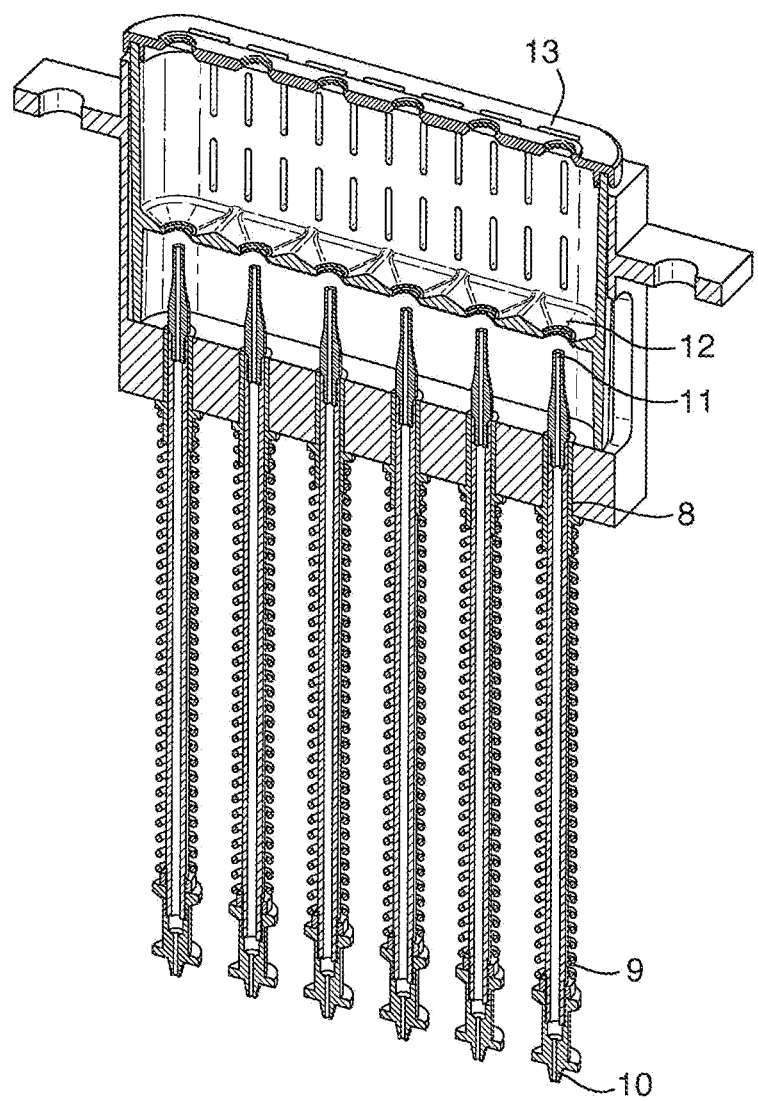
FIG. 2 shows a section through a cartridge holding assembly.

FIG. 2 shows a section through a cartridge holding assembly 3. The cartridge holder 3 preferably comprises a push rod guide bush 8. A push rod adjuster 9 is preferably provided at one end of the push rods 4 together with a vacuum inlet 10. FIG. 2 shows the push rod ends 11 which have not, yet entered the cartridge 1. The cartridge 1 preferably comprises an entry aperture 12 and a bead exit aperture 13. The entry aperture 12 is preferably located on one (i.e. lower) side of the cartridge 1 and the bead exit aperture 13 is preferably located on one opposite (i.e. upper) side of the cartridge 1.

Figure 3:
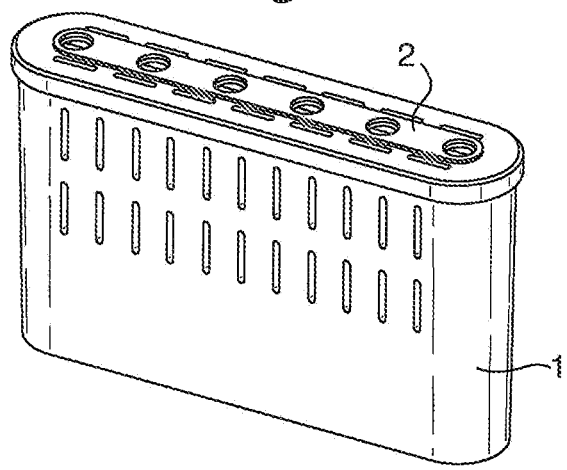
FIG. 3 shows a bead cartridge according to a preferred embodiment.
Figure 4:
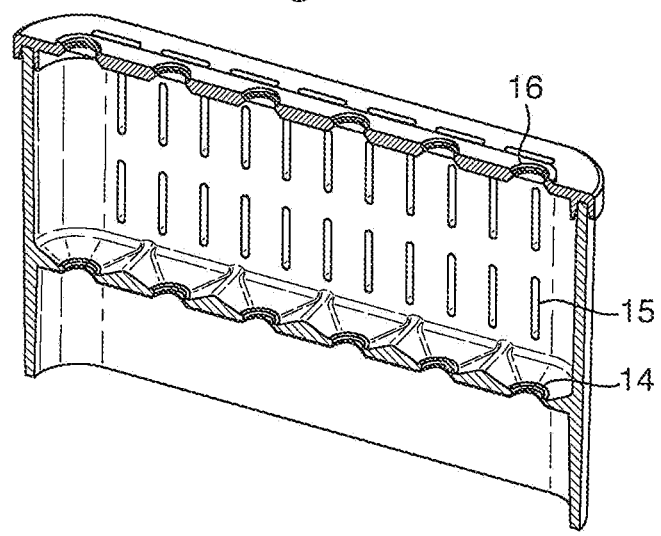
FIG. 4 shows the inside of a bead cartridge according to a preferred embodiment.

FIGS. 3 and 4 show a bead cartridge 1 according to a preferred embodiment of the present invention. The bead cartridge 1 preferably comprises an injection molded disposable housing. The assembly is preferably made up of the cartridge body 1, a cartridge cap 2 having cap apertures 16 and a plurality of silicone membranes 14 provided around apertures in the base of the cartridge body 1. Optionally, a plurality of silicone membranes (not shown) may also be provided around the apertures 16 in the cartridge cap 2. The silicone membranes 14 are preferably molded to the cartridge body 1 and/or the cartridge cap 2 using an over molding process. One or more cartridge vents 15 may be provided in the housing of the cartridge 1.

Figure 5:
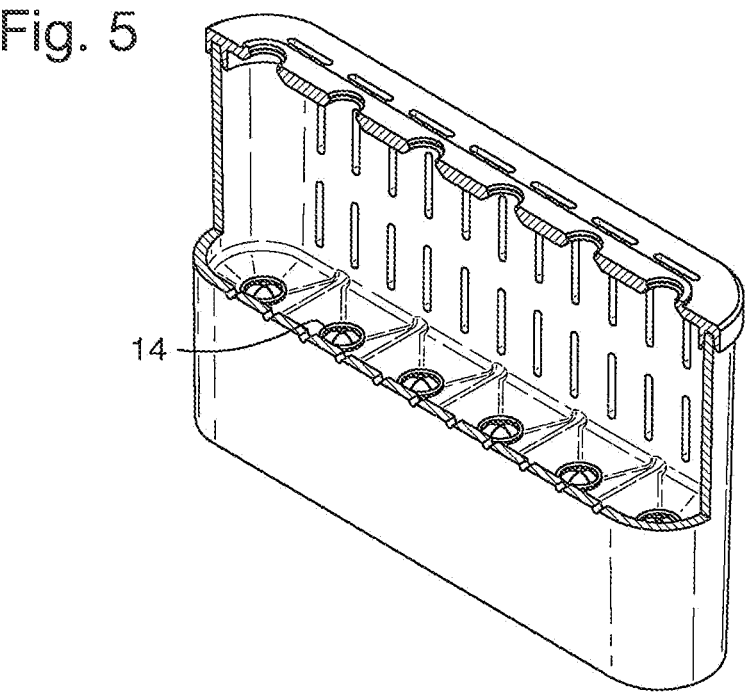
FIG. 5 shows in greater detail silicone membranes in the base of a bead cartridge.

FIG. 5 shows a plurality of silicone membranes 14 provided around apertures in the base of the cartridge 1 in greater detail. The part of the membranes 14 that covers the holes or apertures in the base of the cartridge 1 preferably has cuts or slits molded into it. The molded cuts or slits may, for example, be in the shape of a cross allowing the membrane to fold out of the way when the push rods 4 travel through it. When the push rods 4 withdraw from the base of the cartridge 1, the membranes preferably revert back to their original shape and preferably prevent beads being pulled through the membrane and hence exiting the cartridge 1. The silicone membranes 14 are preferably rigid enough to dislodge any beads inadvertently resting on the ends of the push rods 4.

Figure 6:
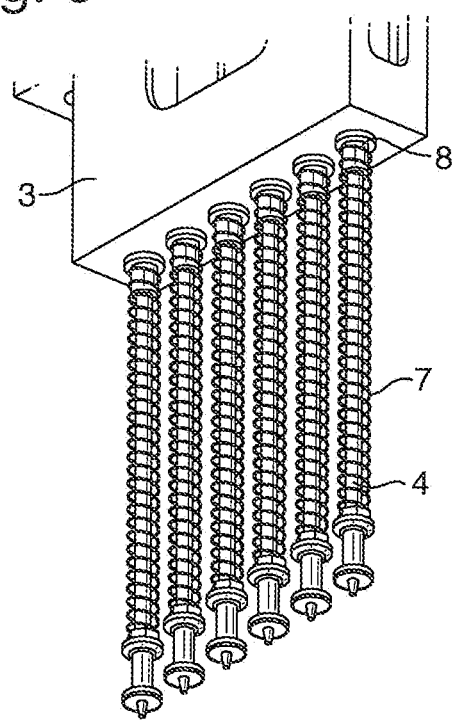
FIG. 6 shows push rods and a cartridge holder assembly.

FIG. 6 shows the base of a cartridge holder assembly 3 in greater detail. The particular embodiment shown in FIG. 6 shows six push rods 4 arranged to pass through the cartridge holder 3. However, other embodiments are contemplated wherein a different number of push rods 4 may be provided. In particular, eight push rods 4 may be provided. The push rods 4 preferably slide in bearing bushes 8 located in a lower surface of the cartridge holder 3. The bearing bushes 8 preferably ensure that the ends of the push rods 4 are located in the correct place relative to the macroplate or sample plate which is preferably arranged above the cartridge holder 3. Return springs 7 preferably ensure that the push rods 4 are at the extent of their travel. This preferably ensures that the push rods 4 are always at the correct height for the device to engage to.

Figure 7:
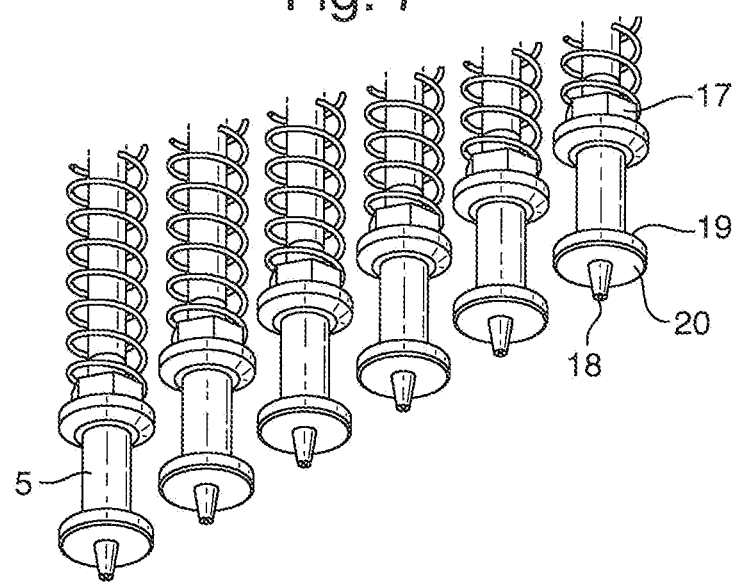
FIG. 7 shows connection bosses at a lower end of push rods in greater detail.

FIG. 7 shows the connection bosses 5 located at the bottom of the push rods 4 in greater detail. The connection bosses 5 are preferably threaded on to the ends of the push rods 4. During assembly the connection bosses 5 are preferably adjusted to the correct overall length and are preferably locked in place by one or more lock nuts 17. The end of the connection bosses 5 preferably have a tapered detail 18 which facilitates engagement of the connection bosses 5 to a lift mechanism of the device. A lower flange 19 of the connection bosses 5 preferably allows a clamp mechanism in the device to clamp down on the connection bosses 5 to ensure that the face 20 of the connection boss 5 is pressed against a seal.

Figure 8:
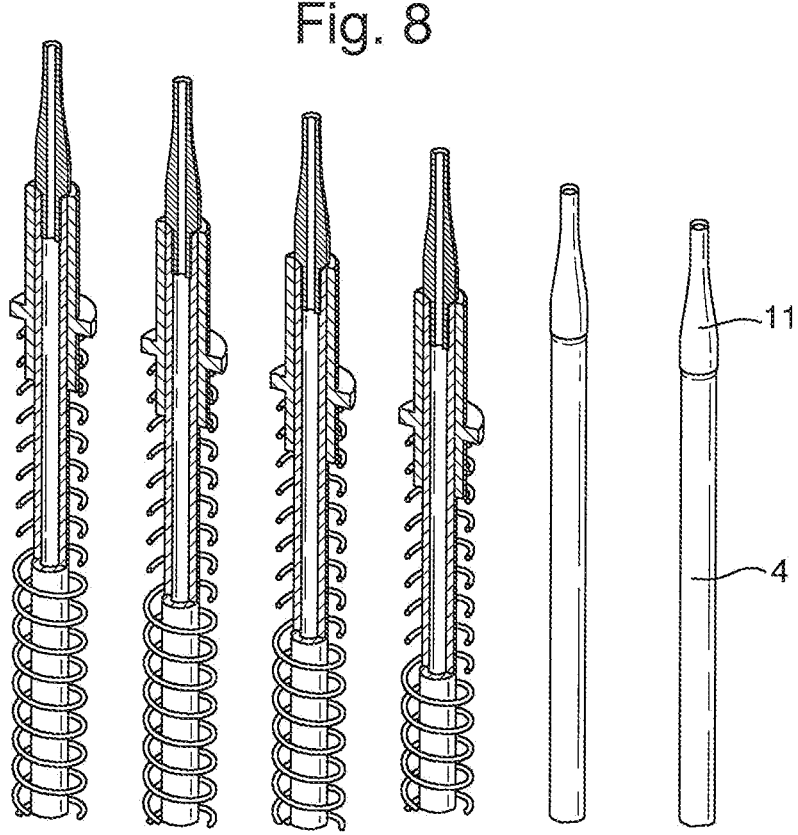
FIG. 8 shows the upper ends of the push rods in greater detail.
Figure 9:
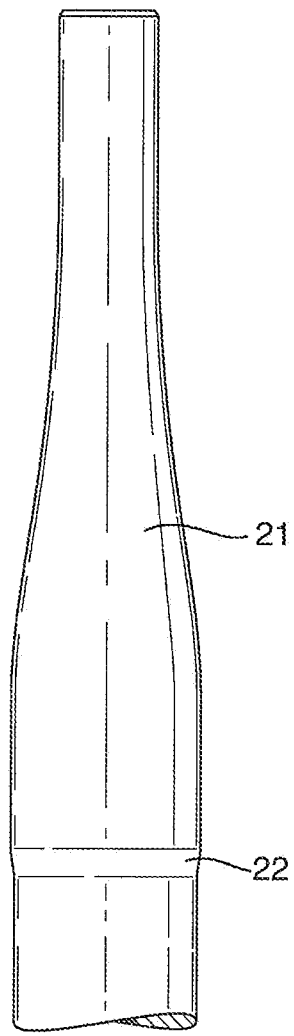
FIG. 9 shows the end of a push rod in greater detail.

FIGS. 8 and 9 show the upper end 11 of the push rods 4 in greater detail. The push rods 4 are preferably stainless steel for strength, wear resistance and corrosion resistance. The push rods 4 preferably have screw-on push rod end 11 which preferably comprise stainless steel and may be titanium nitride coated for wear resistance. The shape of the upper rod ends 11 preferably allows the upper end 11 of the push rods 4 to pass through beads within a cartridge 1 without damaging the beads. According to an embodiment the push rod 4 may have ends which are slightly larger in diameter than the diameter of the rest of the push rods 4. This preferably prevents the push rods 4 from sliding through the bearing bushes 8. At the base of the push rod ends 11 a curve 21 may be provided together with a curved end 22 to ensure that reagent beads are not trapped and/or damaged when the push rods 4 are fully retracted.

Figure 10:
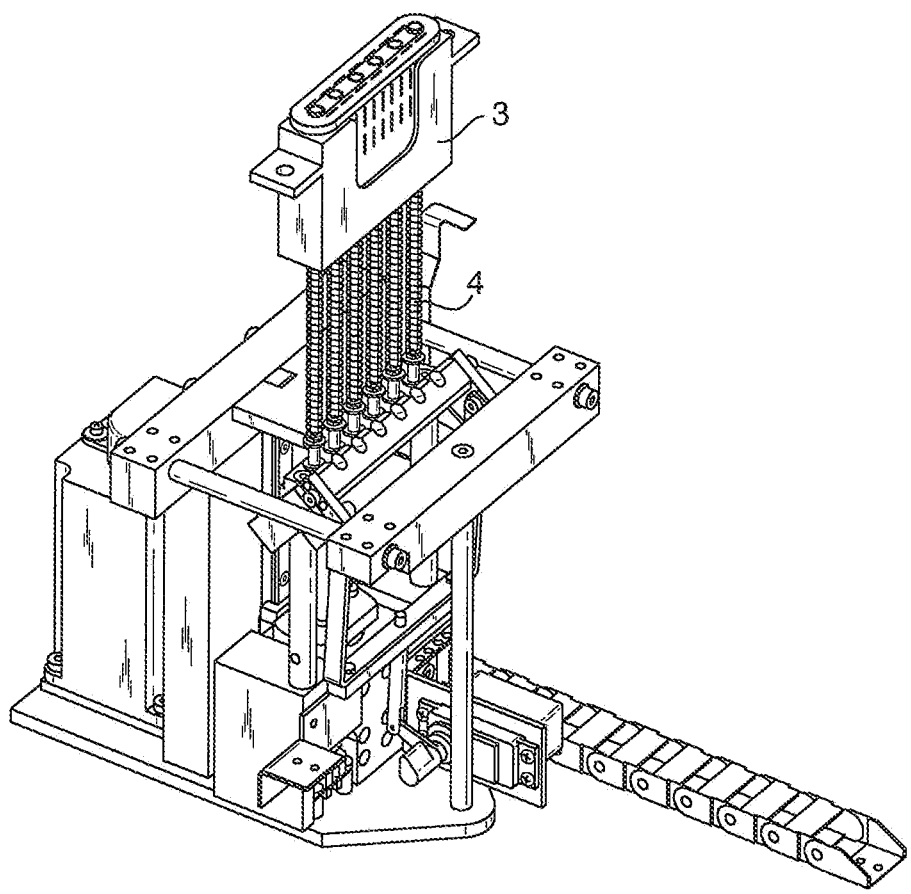
FIG. 10 shows a cartridge holder in a lift mechanism.

FIG. 10 shows a cartridge holder 3 engaged with a lift mechanism according to an embodiment of the present invention. The lift mechanism may comprise a clamp mechanism which engages with the push rods 4.

Figure 11:
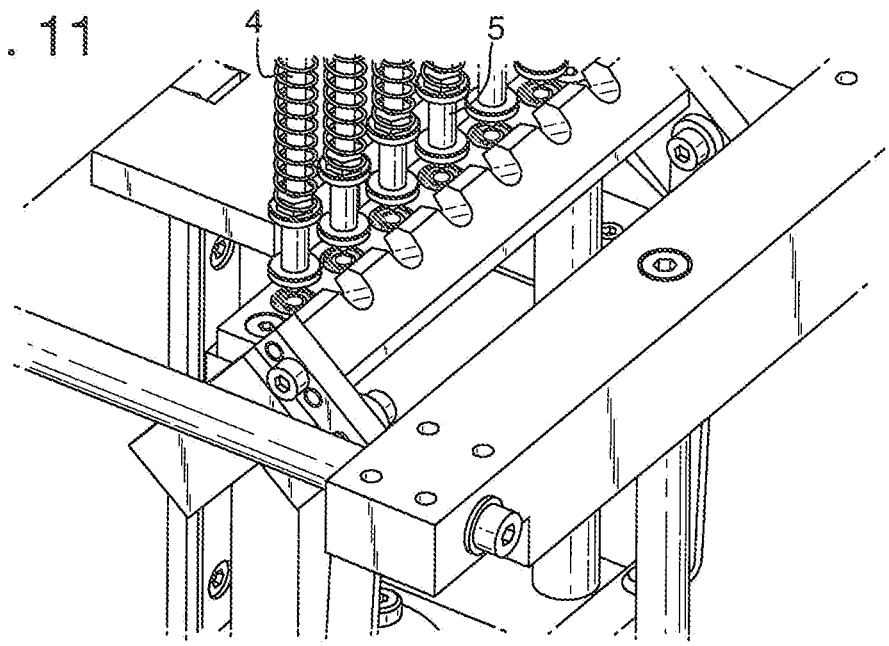
FIG. 11 shows in more detail how the lift mechanism moves into engagement with connection bosses of the push rods.
Figure 12:
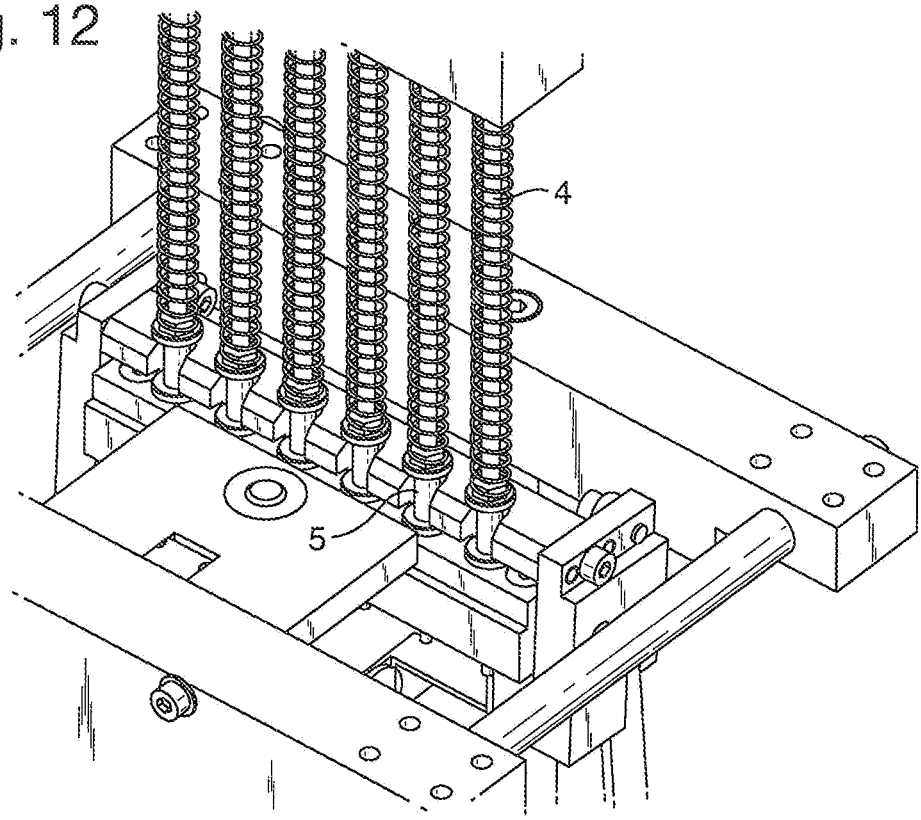
FIG. 12 shows in more detail push rods clamped to the lift mechanism.

FIGS. 11 and 12 shows in more detail the lift mechanism being rotated into position so as to engage with the connection bosses 5 provided at the lower end of the push rods 4. FIG. 11 shows the connection bosses 5 in a position where they are not yet clamped to the lift mechanism. FIG. 12 shows the connection bosses 5 engaged with the lift mechanism.

Although the present invention has been described with reference to preferred embodiments, it will be understood by those skilled in the art that various changes in form and detail may be made without departing from the scope of the invention as set forth in the accompanying claims.

The invention claimed is:

1. A system for inserting reagent or macrobeads into one or more bores of a sample plate comprising:

an insertion device comprising one or more push or insertion rods, wherein said one or more push or insertion rods comprise one or more internal bores;

a cartridge comprising, in use, a plurality of reagent or macrobeads; and a sample plate having an upper surface and a lower surface and one or more bores extending from said upper surface through to said lower surface, wherein said cartridge is located, in use, adjacent and/or below said sample plate and said one or more push or insertion rods is positionable below said sample plate; and wherein said insertion device is arranged and adapted:
(i) to cause said one or more push or insertion rods to enter said cartridge so that each push or insertion rod collects and retains a reagent or macrobead by means of a vacuum, suction or a reduced pressure region; and then
(ii) to cause each of said one or more push or insertion rods to exit said cartridge and insert each said reagent or macrobead into a bore of said sample plate via the lower surface of said sample plate, so that each said reagent or macrobead forms a fluid tight circumferential seal with said bore.

2. A system as claimed in claim 1, wherein said sample plate is arranged so that, in use, an analyte or other sample when dispensed into said sample plate via said upper surface of said sample plate makes fluid contact with an upper portion of said reagent or macrobead which has not been in direct contact with said one or more push or insertion rods.

3. A system as claimed in claim 2, wherein said sample plate is arranged so that a lower portion of said reagent or macrobead which has been in direct contact with said one or more push or insertion rods does not make fluid contact with said analyte or other sample when said analyte or other sample is dispensed into said sample plate via said upper surface of said sample plate.

4. A system as claimed in claim 1, further comprising a vacuum device arranged and adapted to apply or maintain a vacuum, suction or reduced pressure region at an end of said one or more push or insertion rods or said one or more internal bores in said push or insertion rods so as to retain in use a reagent or macrobead on the end of said one or more push or insertion rods whilst said insertion device is in the process of inserting said one or more reagent or macrobeads into said one or more bores of said sample plate.

5. A system as claimed in claim 1, wherein said cartridge comprises one or more membranes or retention members provided in the base of said cartridge and wherein, in use, said one or more push or insertion rods pass through or past said one or more membranes or retention members.

6. A system as claimed in claim 5, wherein in the absence of said one or more push or insertion rods said one or more membranes or retention members close to seal said cartridge and prevent reagent or macrobeads located within the cartridge from exiting said cartridge.

7. A system as claimed in claim 1, wherein said cartridge comprises a removable cap having one or more apertures wherein said one or more push or insertion rods pass through said one or more apertures in the process of inserting said reagent or macrobeads into said one or more bores of said sample plate.

8. A system as claimed in claim 7, wherein said cap comprises one or more membranes or retention members and wherein, in use, said one or more push or insertion rods pass through or past said one or more membranes or retention members in the process of inserting reagent or macrobeads into said one or more bores of said sample plate.

9. A system as claimed in claim 1, further comprising a cartridge holder arranged and adapted to hold said cartridge in position relative to said sample plate.

10. A system as claimed in claim 1, wherein said cartridge comprises an identification symbol or barcode.

11. A system as claimed in claims 10, wherein said cartridge holder comprises an aperture and said identification symbol or barcode is viewable via said aperture in said cartridge holder.

12. A method of inserting reagent or macrobeads into one or more bores of a sample plate comprising:
   providing a cartridge comprising a plurality of reagent or macrobeads;
   providing a sample plate having an upper surface and a lower surface and one or more bores extending from said upper surface through to said lower surface;
   locating said cartridge adjacent and/or below said sample plate;
   causing one or more push or insertion rods to enter said cartridge so that each push or insertion rod collects and retains a reagent or macrobead by means of a vacuum, suction or a reduced pressure region; and then
   causing each of said one or more push or insertion rods to exit said cartridge and insert each said reagent or macrobead into a bore of said sample plate via the lower surface of said sample plate, so that each said reagent or macrobead forms a fluid tight circumferential seal with said bore.

13. A method as claimed in claim 12, further comprising dispensing an analyte or other sample into said sample plate via said upper surface of said sample plate so that said analyte or other sample contacts an upper portion of said reagent or macrobead which has not been in direct contact with said one or more push or insertion rods.

14. A method as claimed in claim 13, further comprising arranging said sample plate so that a lower portion of said reagent or macrobead which has been in direct contact with said one or more push or insertion rods does not make fluid contact with said analyte or other sample when said analyte or other sample is dispensed into said sample plate via said upper surface of said sample plate.

* * * * *